(12) United States Patent
Bhargava et al.

(10) Patent No.: US 11,161,055 B2
(45) Date of Patent: *Nov. 2, 2021

(54) USE OF TOP DIVIDING WALL IN ISOMERIZATION UNIT

(71) Applicant: Sulzer Management AG, Winterthur (CH)

(72) Inventors: Manish Bhargava, Katy, TX (US); Roomi Kalita, Houston, TX (US); Joseph C. Gentry, Houston, TX (US)

(73) Assignee: SULZER MANAGEMENT AG, Winterthur (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/648,447

(22) PCT Filed: Sep. 18, 2018

(86) PCT No.: PCT/US2018/051584
§ 371 (c)(1),
(2) Date: Mar. 18, 2020

(87) PCT Pub. No.: WO2019/060324
PCT Pub. Date: Mar. 28, 2019

(65) Prior Publication Data
US 2020/0223771 A1    Jul. 16, 2020

Related U.S. Application Data

(60) Provisional application No. 62/560,569, filed on Sep. 19, 2017.

(51) Int. Cl.
*B01D 3/14* (2006.01)
*C07C 7/00* (2006.01)
(Continued)

(52) U.S. Cl.
CPC ............ *B01D 3/141* (2013.01); *B01D 3/009* (2013.01); *B01D 3/06* (2013.01); *B01D 3/148* (2013.01);
(Continued)

(58) Field of Classification Search
CPC ... C07C 5/22–2293; C07C 7/005; C07C 7/11; C07C 7/04; C07C 5/2702;
(Continued)

(56) References Cited

U.S. PATENT DOCUMENTS

| 6,395,950 B1 * | 5/2002 | Rice | B01D 3/141 585/734 |
| 6,552,242 B1 * | 4/2003 | Rice | B01D 3/141 208/347 |

(Continued)

FOREIGN PATENT DOCUMENTS

CN          207822549 U      9/2018

OTHER PUBLICATIONS

International Search Report and Written Opinion for PCT/US18/51584; dated Mar. 15, 2019; Authorized Officer Lee W. Young; 7 pages.

*Primary Examiner* — Ali Z Fadhel
(74) *Attorney, Agent, or Firm* — Global IP Counselors, LLP

(57) ABSTRACT

The invention is directed to a combined naphtha hydrotreating (NHT) and isomerization process scheme, which includes dividing wall columns (DWC) that replace multiple distillation columns and allow optimized heat integration within the system. The disclosed design provides reductions in both capital and energy costs compared to conventional schemes.

11 Claims, 3 Drawing Sheets

(51) Int. Cl.
*C07C 7/11* (2006.01)
*C07C 7/04* (2006.01)
*B01J 8/04* (2006.01)
*B01J 8/06* (2006.01)
*C07C 5/27* (2006.01)
*C10G 67/02* (2006.01)
*C10G 7/02* (2006.01)
*C10G 7/00* (2006.01)
*C10G 45/58* (2006.01)
*B01D 3/00* (2006.01)
*B01D 3/06* (2006.01)
*B01D 3/32* (2006.01)
*B01D 5/00* (2006.01)
*C10G 67/14* (2006.01)

(52) U.S. Cl.
CPC .......... *B01D 3/322* (2013.01); *B01D 5/0063* (2013.01); *B01J 8/0484* (2013.01); *B01J 8/0488* (2013.01); *B01J 8/0492* (2013.01); *B01J 8/065* (2013.01); *C07C 5/2702* (2013.01); *C07C 7/005* (2013.01); *C07C 7/04* (2013.01); *C07C 7/11* (2013.01); *C10G 7/00* (2013.01); *C10G 7/02* (2013.01); *C10G 45/58* (2013.01); *C10G 67/02* (2013.01); *C10G 67/14* (2013.01); *B01J 2208/025* (2013.01); *C10G 2300/1044* (2013.01)

(58) Field of Classification Search
CPC ........ B01D 3/141; B01D 3/148; B01J 8/0492; B01J 8/065; B01J 8/0484; B01J 8/0488; B01J 2208/025; C10G 45/58; C10G 67/02; C10G 7/00; C10G 7/02
See application file for complete search history.

(56) References Cited

U.S. PATENT DOCUMENTS

| | | | | |
|---|---|---|---|---|
| 6,759,563 | B1* | 7/2004 | Hibbs | C07C 5/2791 585/734 |
| 6,927,314 | B1* | 8/2005 | Schultz | B01D 3/141 585/734 |
| 2004/0236139 | A1* | 11/2004 | Schal | C07C 263/20 558/420 |
| 2006/0287563 | A1* | 12/2006 | Schultz | C07C 6/123 585/481 |
| 2012/0271071 | A1* | 10/2012 | Haizmann | C07C 5/2732 585/1 |
| 2012/0271084 | A1* | 10/2012 | Haizmann | C07C 6/126 585/323 |
| 2015/0211790 | A1* | 7/2015 | Bhargava | B01D 3/40 62/625 |
| 2015/0251972 | A1* | 9/2015 | Shecterle | C10G 35/00 585/302 |
| 2015/0376086 | A1* | 12/2015 | Tinger | C07C 2/864 585/314 |
| 2016/0046544 | A1* | 2/2016 | Molinier | C07C 5/2732 585/319 |
| 2016/0200989 | A1 | 7/2016 | Noureldin et al. | |
| 2016/0272558 | A1* | 9/2016 | Bender | C07C 5/2729 |
| 2016/0318827 | A1* | 11/2016 | Tinger | B01D 3/143 |
| 2017/0050899 | A1* | 2/2017 | Tinger | B01D 3/141 |
| 2017/0210682 | A1* | 7/2017 | Dreux | C07C 7/04 |
| 2017/0292080 | A1* | 10/2017 | Garcia | C10G 67/02 |
| 2018/0093932 | A1* | 4/2018 | Pednekar | C07C 5/2702 |
| 2018/0282244 | A1* | 10/2018 | Kockler | C07C 5/2702 |
| 2018/0282245 | A1* | 10/2018 | Kockler | C07C 5/2732 |

* cited by examiner

US 11,161,055 B2

USE OF TOP DIVIDING WALL IN ISOMERIZATION UNIT

CROSS-REFERENCES TO RELATED APPLICATIONS

This Application claims the benefit under 35 U.S.C. § 119(e) of U.S. Provisional Pat. App. Ser. No. 62/560,569 filed Sep. 19, 2017, which is incorporated herein by reference in its entirety as if fully set forth herein.

FIELD OF THE INVENTION

The claimed invention relates generally to top dividing wall columns and more particularly, but not by way of limitation, to an improved isomerization unit that reduces cost and increases efficiency.

BACKGROUND OF THE INVENTION

Isomerization units are important to refineries for providing a simple process of upgrading traditional low octane gasoline blending stocks. Additionally, refineries are able to regulate benzene content by hydrogenation of the benzene fraction. A naphtha hydrotreating (NHT) and isomerization unit 100 is comprised of multiple conventional distillation columns as shown in FIG. 1. A feed stream from an NHT reactor is sent to a first stabilizer column 102. The first stabilizer column 102 removes non-condensable components from the feed stream as off-gas. A stabilized bottoms product stream is fed from the first stabilizer column 102 to a naphtha splitter column 104. The naphtha splitter column 104 separates the stabilized bottom product into a light naphtha overhead stream and heavy naphtha bottoms stream.

The light naphtha overhead stream is comprised mainly of $C_5$-$C_6$ components. Typically, the light naphtha overhead stream is fed to a deisopentanizer column 106, which concentrates i-$C_5$ as an overhead stream of the deisopentanizer column 106. The remaining $C_5$-$C_6$ components are obtained as a bottoms stream of the deisopentanizer column 106 and are fed to an isomerization reactor 108 for octane upgrading. Following isomerization, unstable isomerate from the isomerization reactor 108 is further processed in a second stabilizer column 110. Subsequently, light hydrocarbons are removed in an overhead stream as off-gas and stable isomerate is sent to a depentanizer column 112 to remove a concentrated stream of $C_5$ components.

A $C_5$ rich stream from the depentanizer column 112 is recycled back to the deisopentanizer column 106 upstream to remove i-$C_5$ product. The bottoms product stream from the depentanizer column 112 is fed to a deisohexanizer column 114. A $C_6$ isomerate product stream is removed from the deisohexanizer column 114 as an overhead stream and a heavy isomerate product stream (mainly $C_{7+}$ cut) is removed from the deisohexanizer column 114 as bottoms stream. An n-$C_6$ rich cut is removed as a side cut from the deisohexanizer column 114 and is recycled to the isomerization reactor.

The prior art system 100 of FIG. 1 possesses several disadvantages. The first and second stabilizer columns 102, 110 in the prior art system 100 operate at relatively high pressures (~100 psig and ~160 psig respectively in this case). Due to the partial condensation used in conventional stabilizers, liquid losses to off gas are high. Similarly, the naphtha splitter column 104 also operates at a high pressure (~75 psig). Consequently, the column reboilers operate on moderately expensive medium pressure (MP) steams.

Furthermore, due to the number of columns involved, typical high operating temperatures, and high operating pressures observed in the various stages of the process, a conventional isomerization unit can be a costly and energy-intensive operation. With demand for isomerization units ramping up in the refining industry, improving the process scheme to make it less costly and more efficient is desirable.

SUMMARY OF THE INVENTION

Dividing wall column (DWC) technology enables improvements to the efficiency and cost of traditional isomerization process schemes. An embodiment of the invention is directed to a process wherein isomerization is used to obtain high octane $C_5$ and $C_6$ components for gasoline blending. An embodiment of the invention includes an application wherein a multi-column isomerization configuration is replaced with lesser number of distillation columns utilizing a DWC concept. Due to a combination of lower operating column pressures and improved heat integration within the system, DWC configurations consume significantly less energy and reduce the cost of heating.

An embodiment of the invention encompasses hydrotreating reactor stabilizer columns, wherein a first stabilizer column and a downstream naphtha splitter column are combined into a single top dividing wall column (e.g., See FIGS. 2 and 3). Such an arrangement produces the similar number of products, while reducing the number of columns from two to one. The new hybrid column operates at the same pressure as a conventional stabilizer.

In some embodiments, a DWC includes a dividing wall positioned in a top section of the DWC to form two top halves, wherein the two top halves act as independent columns For example, the first stabilizer column and naphtha splitter column of the prior art system of FIG. 1 are combined into a top dividing wall column (e.g., see FIGS. 2 and 3). In this particular DWC, the side of the DWC where the stream enters operates as an absorber. A lean naphtha stream is used as the absorption medium. This lean naphtha stream can be obtained either from a heavier bottoms of the DWC column or from another nearby column within the same complex. The other side of the DWC operates like a typical distillation column. Hence, an embodiment of the invention encompasses such columns, wherein both distillation and absorption are carried out within the same column.

Similarly, the depentanizer and deisohexanizer columns of the prior art system of FIG. 1 can also be combined into a top DWC (e.g., see FIGS. 2 and 4). For this DWC column, a top portion of the DWC behaves as two separation zones. One side acts as a depentanizer to remove $C_5$ components, while the other side operates as a deisohexanizer column to recover light (mainly $C_6$ isomerate) and heavy isomerate ($C_7$ and heavier) products.

In some embodiments, the isomerization stabilizer is operated at a lower pressure than the prior art system of FIG. 1. For example, the pressure may be around 75 psig, as compared to around 160 psig for the second stabilizer column of the prior art system of FIG. 1. The operating pressure has been selected such that, compared to the prior art system of FIG. 1, the second stabilizer column operates with lower temperature heating utility (low pressure steam in this case). Additionally, some reboiling duty to the second stabilizer column is obtained by heat integration with reactor effluent bottoms from the isomerization reactor.

In some embodiments, the DWC comprising the first stabilizer column and the naphtha splitter column is operated at a high pressure (~100 psig) as well. This arrangement compensates for the lower operating pressure of the downstream second stabilizer column. The valuable $C_5$ components lost in the latter system is captured in the upstream DWC column by means of absorption using a lean naphtha stream. Furthermore, due to higher temperatures, this arrangement facilitates heat integration with the deisopentanizer column.

In some embodiments, a packed flash drum is used wherein off-gas from the second stabilizer is stripped using a part of the heavy naphtha bottoms from DWC column that combines the first stabilizer column and the naphtha splitter column. The residual lean naphtha stream is obtained as the liquid product from the drum and used as the absorption medium in the configuration.

In some embodiments, the system utilizes a combination of low pressure (LP) and medium (MP) steam by applying DWC technology to the configuration provides significant reduction in utility costs as compared to the prior art system of FIG. 1.

DETAILED DESCRIPTION OF EXEMPLARY EMBODIMENTS

Embodiments of the invention are directed to an isomerization process wherein individual columns are replaced and/or combined together using DWC technology with the objective of minimizing utility consumption.

Figure 2:
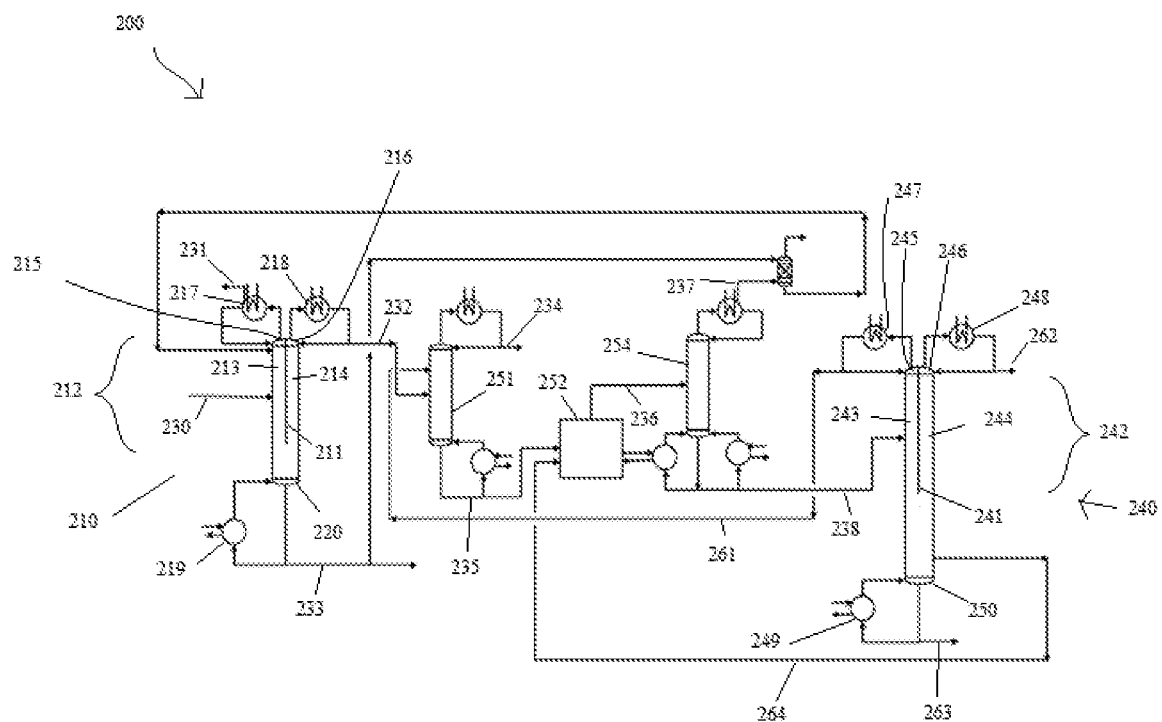
FIG. 2 represents a process scheme in accordance with an embodiment of the invention for using DWC technology in a naphtha hydrotreating and isomerization unit.

Referring now to FIG. 2, an isomerization process scheme 200 is shown. Scheme 200 includes a first divided wall column (DWC) 210 and a second DWC 240. First DWC 210 includes a top dividing wall 211 that divides a top portion 212 of first DWC 210 into a first side 213 and a second side 214. In the embodiment illustrated in FIG. 2, first side 213 is configured to operate as a stabilizer column and second side 214 is configured to operate as a naphtha splitter column. In some embodiments, first side 213 includes a first overheads section 215 and second side 214 includes a second overheads section 216. A first condenser 217 is coupled to first overheads section 215 and is configured to condense overheads received therefrom. Reflux from first condenser 217 can be fed back to first overheads section 215. A second condenser 218 is coupled to second overheads section 216 and is configured to condense overheads received therefrom. Reflux from second condenser 218 can be fed back to second overheads section 216. A bottoms reboiler 219 is coupled to first DWC 210 and is configured to receive a bottoms stream from first DWC 210 and to return a heated stream back to a bottoms section 220 of first DWC 210.

Second DWC 240 includes a top dividing wall 241 that divides a top portion 242 of second DWC 240 into a first side 243 and a second side 244. In the embodiment illustrated in FIG. 2, first side 243 is configured to operate as a depentanizer column and second side 244 is configured to operate as a deisohexanizer column. In some embodiments, first side 243 includes a first overheads section 245 and second side 244 includes a second overheads section 246. A first condenser 247 is coupled to first overheads section 245 and is configured to condense overheads received therefrom. Reflux from first condenser 247 can be fed back to first overheads section 245. A second condenser 248 is coupled to second overheads section 246 and is configured to condense overheads received therefrom. Reflux from second condenser 248 can be fed back to second overheads section 246. A bottoms reboiler 249 is coupled to second DWC 240 and is configured to receive a bottoms stream from second DWC 240 and to return a heated stream back to a bottoms section 250 of second DWC 240.

An exemplary process flow for scheme 200 begins by feeding a stream 230 to first side 213 of first DWC 210. In the embodiment of FIG. 2, first side 213 is a stabilizer and second side 214 is a naphtha splitter. In some embodiments, stream 230 is sourced from a naphtha hydrotreating reactor. First side 213 removes non-condensable components from stream 230 as off-gas stream 231. A stabilized bottoms product descends first side 213 and enters second side 214. Second side 214 separates the stabilized bottom product from first side 213 into a light naphtha overhead stream 232 and heavy naphtha bottoms stream 233.

The light naphtha overhead stream 232 is comprised mainly of $C_5$-$C_6$ components. Light naphtha overhead stream 232 is fed to a deisopentanizer column 251, which concentrates i-$C_5$ as an overhead stream 234. The remaining $C_5$-$C_6$ components are obtained as a bottoms stream 235 of deisopentanizer column 251 and are fed to an isomerization reactor 252 for octane upgrading via isomerization reactions. A stream 236 containing unstable isomerate from isomerization reactor 252 is further processed in a stabilizer column 254. Light hydrocarbons are removed in an overhead stream 237 as off-gas and a stream 238 containing stable isomerate is sent to first side 243 of second DWC 240 to remove a concentrated stream of $C_5$ components.

In the embodiment of FIG. 2, first side 243 is a depentanizer and second side 244 is a deisohexanizer An overheads stream 261 that is rich in $C_5$ is recycled from the first overheads section 245 of second DWC 240 to deisopentanizer column 251 upstream to remove i-$C_5$ product. A bottoms product stream descends first side 243 and enters second side 244. A $C_6$ isomerate product stream 262 is removed from second DWC 240 as an overhead stream and a heavy isomerate product stream 263 (mainly $C_{7+}$ cut) is removed from second DWC 240 as bottoms stream. An n-$C_6$ rich stream 264 is removed as a side cut from second DWC 240 and is recycled to the isomerization reactor 252.

Figure 1:
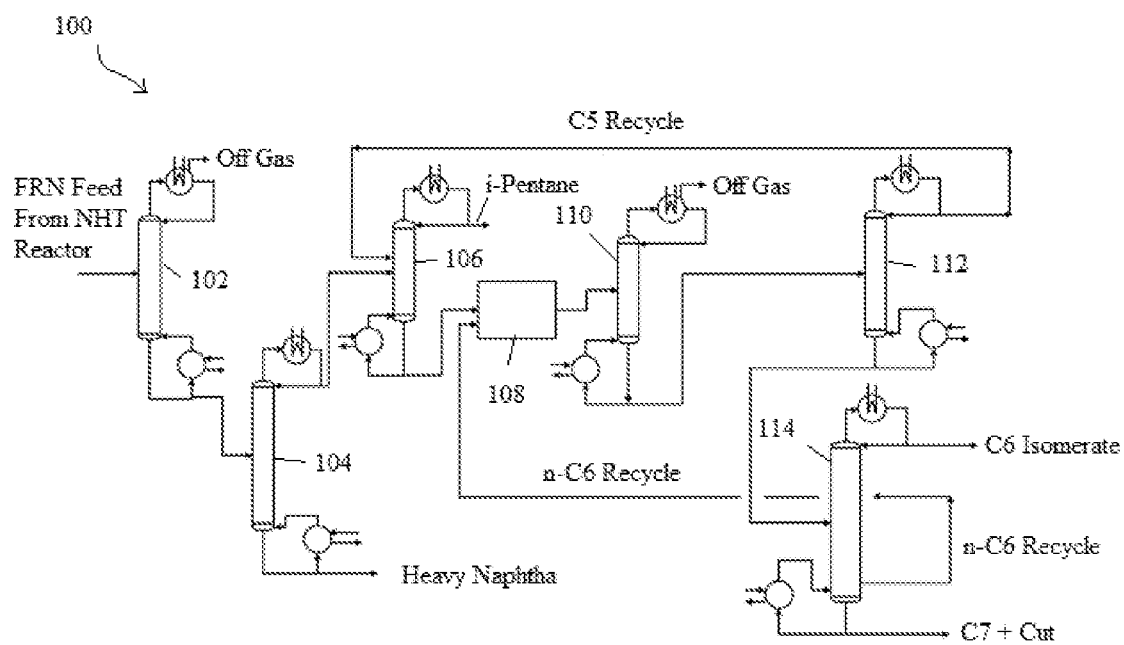
FIG. 1 represents a prior art system of a combined naphtha hydrotreating and isomerization unit.
Figure 3:
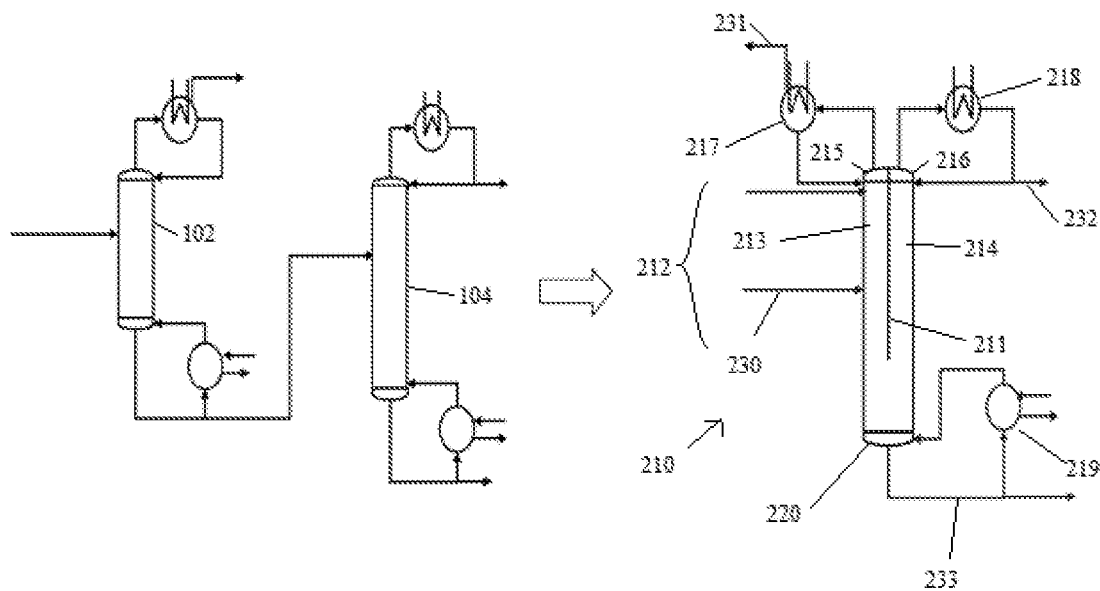
FIG. 3 represents a process scheme in accordance with an embodiment of the invention for a top DWC stabilizer/naphtha splitter design.

FIG. 3 is a side-by-side comparison of columns 102 and 104 of FIG. 1 with first DWC 210 of FIG. 2. Top dividing wall 211 segregates the top portion 212 of first DWC 210 into first side 213 and second side 214, namely the prefractionation side and the product side for reference. The process scheme is designed to remove the non-condensable as off-gas stream 231. Additionally, the scheme concentrates middle boiling components ($C_5$-$C_7$) as light naphtha overhead stream 232 on the other side, while the heaviest boiling components (heavy naphtha) are recovered at the bottom of the column as heavy naphtha bottoms stream 233. On the feed side of the top dividing wall 211, a lean naphtha stream reduces the loss of valuable $C_5$ components into the off-gas by means of absorption. On the product side of top dividing wall 211, the middle boiling $C_5$-$C_7$ components move to the top and the heavy boiling components move downwards. The scheme, hence, performs a combination of distillation and absorption within the same column. Moreover, first condenser 217 on the absorption side is a partial water-cooled condenser, while the second condenser 218 on the distillation side is a total condenser using an air-cooled exchanger.

DWC 212 operates at a high operating pressure of 100 psig and utilizes MP steam as the heating medium in bottoms reboiler 219 (e.g., a thermosiphon reboiler). The high temperature of the column allows heat integration with the downstream deisopentanizer column 251 that operates at a significantly lower pressure.

Deisopentanizer column 251 is a conventional distillation column which removes an isopentane concentrated stream at the top (overhead stream 234). A reboiler of deisopentanizer column 251 utilizes LP steam, while another reboiler is heat integrated with the hot overhead $C_5$-$C_7$ vapors from the upstream DWC 212.

Figure 4:
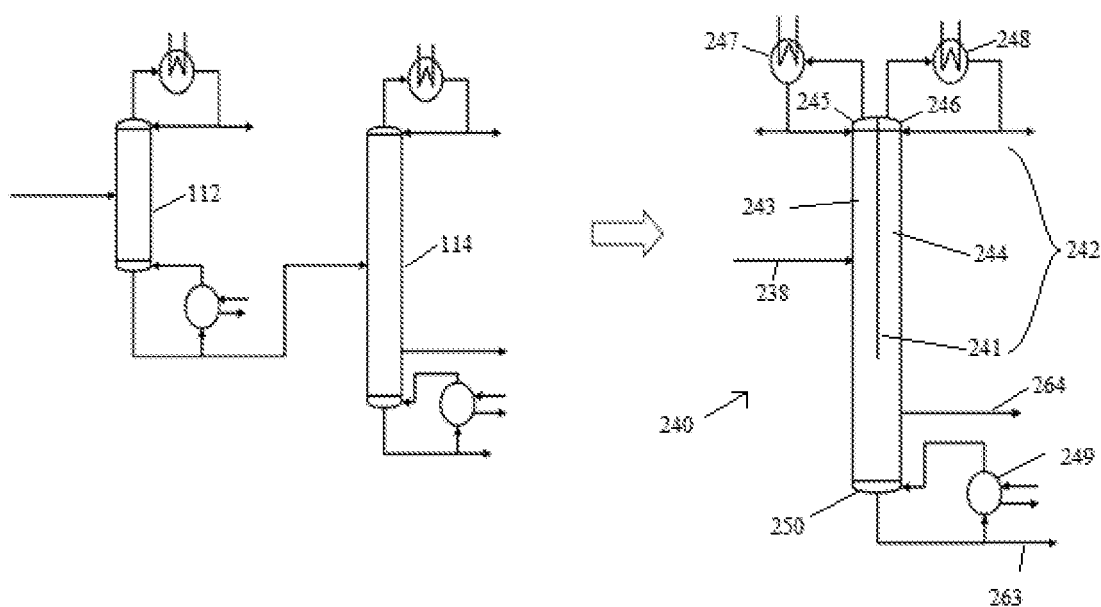
FIG. 4 represents a process scheme in accordance with an embodiment of the invention for a top DWC depentanizer/deisohexanizer design.

FIG. 4 is a side-by-side comparison of columns 112 and 114 of FIG. 1 with second DWC 240 of FIG. 2. Second DWC 240 separates four product streams: a $C_5$ recycle stream 261, $C_6$ isomerate stream 262, and $C_7+$ stream 263 along with a n-$C_6$ recycle stream 264. Two total condensers 247, 248 are available on both sides of top dividing wall 241. In some embodiments, condensers 247, 248 are air-cooled exchangers. Bottoms reboiler 249 at the bottom of second DWC 240 operates on LP steam.

In embodiments of the invention, column overhead pressures are maintained via a pressure controller on the overhead vapor product line. The pre-fractionation side has reflux coming from the overhead condenser.

Table 1 below highlights energy and cost savings of scheme 200 versus prior art system 100.

TABLE 1

| Parameters | Units | Conventional Design | DWC Design |
|---|---|---|---|
| No. of columns | — | 6 | 4 |
| Energy Savings | % | Base | 30% of Base |
| Capital Cost | % | Base | 70% of Base |

Table 2 below highlights operating parameteres of scheme 200 versus prior art system 100.

TABLE 2

| | | Conventional Design NHT Stabilizer | DWC Design Stabilizer/Naphtha Splitter |
|---|---|---|---|
| Operating pressure | psig | 100 | 100 |
| Reboiler utility | | MP Steam | MP steam |
| | | Naphtha Splitter | |
| Operating pressure | psig | 75 | — |
| Reboiler utility | | MP Steam | — |
| | | Isomerization Stabilizer | Isomerization Stabilizer |
| Operating pressure | psig | 150 | 75 |
| Reboiler utility | | MP Steam | LP Steam/Heat integration with reactor effluent |
| | | Depentanizer | Depentanizer/ Deisohexanizer |
| Operating pressure | psig | 20 | 20 |
| Reboiler utility | | LP Steam | LP Steam |
| | | Deisohexanizer | — |
| Operating pressure | psig | 7 | — |
| Reboiler utility | | LP Steam | — |

What is claimed is:

1. An isomerization unit comprising:
a first dividing wall column comprising:
  a line configured to receive a feed of naphtha;
  a first side configured as a stabilizer column;
  a first condenser configured to reflux a portion of a first overheads stream from the first side of the first dividing wall column to a first overheads section of the first side of the first dividing wall column;
  a second side configured as a naphtha splitter column;
  a second condenser configured to reflux a portion of a second overheads stream from the second side of the first dividing wall column to a second overheads section of the second side of the first dividing wall column; and
  a first top dividing wall that separates the first side of the first dividing wall column and the second side of the first dividing wall column; and
a second dividing wall column comprising:
  a first side configured as a depentanizer column;
  a third condenser configured to reflux a portion of a third overheads stream from the first side of the second dividing wall column to a third overheads section of the first side of the second dividing wall column;
  a second side configured as a deisohexanizer column
  a fourth condenser configured to reflux a portion of a fourth overheads stream from the second side of the second dividing wall column to a fourth overheads section of the second side of the second dividing wall column; and
  a second top dividing wall that separates the first side of the second dividing wall column and the second side of the second dividing wall column.

2. The isomerization unit of claim 1, further comprising:
a deisopentanizer column coupled to the first dividing wall column configured to receive a light naphtha overhead stream from the second side of the first dividing wall column;
an isomerization reactor coupled to the deisopentanizer column and configured to receive a bottoms stream from the deisopentanizer column; and
a stabilizer column coupled to the isomerization reactor and configured to receive a stream comprising unstable isomerate from the isomerization reactor and to feed stable isomerate to the second dividing wall column.

3. The isomerization unit of claim 1, wherein the first dividing wall column comprises a first bottoms reboiler configured to receive a first bottoms stream from the first dividing wall column and to feed a portion of the first bottoms stream back to the first dividing wall column.

4. The isomerization unit of claim 1, wherein the second dividing wall column comprises a second bottoms reboiler configured to receive a second bottoms stream from the second dividing wall column and to feed a portion of the second bottoms stream back to the second dividing wall column.

5. The isomerization unit of claim 1, wherein the second dividing wall column includes a side cut from a position near a bottom of the second dividing wall column that does not contain the second top dividing wall.

6. The isomerization unit of claim 1, further comprising a packed flash drum coupled to the first dividing wall column and configured to receive a third bottoms stream from the first dividing wall column and an off-gas stream from a stabilizer column to generate a lean solvent that is fed back to the first dividing wall column.

7. An isomerization method being performed in an isomerization unit of claim 1, wherein a naphtha stream is provided to the first dividing wall column, wherein the method comprises the following steps:
- processing the naphtha stream with the first dividing wall column to produce an off-gas stream of non-condensable components, a light naphtha overhead stream with the second side of the first dividing wall column and a heavy naphtha bottoms product; and
- producing, via the second dividing wall column, a first stream comprising $C_6$ isomerate product and a second stream comprising a heavy isomerate product.

8. The method of claim 7, wherein the first dividing wall column comprises a bottoms reboiler configured to receive a first bottoms stream from the first dividing wall column and to feed a portion of the first bottoms stream back to the first dividing wall column.

9. The method of claim 7, wherein the second dividing wall column comprises a bottoms reboiler configured to receive a second bottoms stream from the second dividing wall column and to feed a portion of the second bottoms stream back to the second dividing wall column.

10. The method of claim 7, wherein the second dividing wall column includes a side cut from a position near a bottom of the second dividing wall column that does not contain the second top dividing wall.

11. The method of claim 7, further comprising feeding a third bottoms stream from the first dividing wall column and an off-gas stream from the stabilizer column to a packed flash drum to generate a lean solvent that is fed back to the first dividing wall column.

\* \* \* \* \*